United States Patent [19]

Bruzzese et al.

[11] 4,237,117

[45] Dec. 2, 1980

[54] METHOD FOR THE TREATMENT OF BENIGN PROSTATIC HYPERTROPHY

[75] Inventors: Tiberio Bruzzese; Lorenzo Ferrari, both of Milan, Italy

[73] Assignee: Spa-Societa Prodotti Antibiotici S.p.A., Milan, Italy

[21] Appl. No.: 82,403

[22] Filed: Oct. 5, 1979

Related U.S. Application Data

[63] Continuation-in-part of Ser. No. 957,870, Nov. 6, 1978, abandoned.

[51] Int. Cl.³ ............................................... A61K 35/00
[52] U.S. Cl. ....................................................... 424/122
[58] Field of Search ......................................... 424/122

[56] References Cited

U.S. PATENT DOCUMENTS

| | | | |
|---|---|---|---|
| 3,773,925 | 11/1973 | Bruzzese et al. | 424/122 |
| 3,780,173 | 12/1973 | Bruzzese et al. | 424/122 |
| 3,961,047 | 6/1976 | Bruzzese et al. | 424/122 |
| 3,961,048 | 6/1976 | Delliacqua et al. | 424/122 |
| 4,017,603 | 4/1977 | Ferrari et al. | 424/122 |

*Primary Examiner*—Jerome D. Goldberg
*Attorney, Agent, or Firm*—Wenderoth, Lind & Ponack

[57] ABSTRACT

The present invention is concerned with a method for the treatment of benign prostatic hypertrophy in male humans, comprising administering an effective amount of a compound selected from the group consisting of partricin, $C_1$-$C_6$ alkyl ester of partricin and $C_1$-$C_6$ alkyl ester of N-mono- and N,N-disubstituted partricin, the N-substituents being $C_1$-$C_6$ alkyl or carboxylic acyl, to a human male suffering from benign prostatic hypertrophy.

5 Claims, No Drawings

METHOD FOR THE TREATMENT OF BENIGN PROSTATIC HYPERTROPHY

CROSS-REFERENCE TO RELATED APPLICATION

This application is a continuation-in-part of application Ser. No. 957,870, filed Nov. 6, 1978, now abandoned.

BACKGROUND OF THE INVENTION

U.S. Pat. No. 3,773,925 describes and claims the base substance partricin, a heptaene antibiotic produced by the metabolism of a particular strain of *Streptomyces aureofaciens* and endowed with a high antifungal and antiprotozoal activity.

U.S. Pat. No. 3,780,173 describes and claims the methyl ester of partricin and U.S. Pat. No. 3,961,047 describes and claims alkyl esters of N-alkyl and N-acyl derivatives of partricin. Furthermore, water-soluble complexes of partricin and partricin derivatives with particular surfactant agents are described and claimed in U.S. Pat. Nos. 3,961,048 and 4,017,603. All the above-mentioned derivatives of partricin and water-soluble complexes thereof are systemically less toxic than partricin itself, whilst the anti-infective activity varies from compound to compound, optimum activity being found in the case of partricin methyl ester (USAN mepartricin) which, though substantially less toxic than partricin, has an almost unchanged antiprotozoal activity and is also far more active against pathogenic fungi.

In view of these properties, mepartricin is widely used in clinical practice for the local treatment of vaginal infections. Another partricin derivative of particular interest is the 1:2 w/w mepartricin-sodium lauryl sulphate complex which, while keeping the microbiological characteristics of mepartricin unaltered, has the property of being water-soluble and, as such, can be administered orally for the systemic treatment of various fungal and protozoal infections.

We have now discovered that, apart from an anti-infective activity, partricin and its derivatives are effective in the treatment of prostatic hypertrophy, reducing the glandular dimensions and modifying the hypertrophic picture so as to return the organ to its normal size and appearance. This action, although related to the antibiotic activity, does not depend on this but is particularly due to the chemical structure.

It is an object of the present invention to provide a clinically very efficient method for the treatment of prostatic hypertrophy.

Another object of the present invention is to provide a composition for the treatment of prostatic hypertrophy.

Benign prostatic hypertrophy (BPH) consists in a glandular hyperplasia resulting in the formation of new structures of the prostatic parenchyma and of the periurethral glands. To a certain extent, it can be considered as being a general phenomenon of advanced age which is susceptible of anomalous evolution. According to some authors, the incidence of clinically documented glandular hyperplasia affects approximately 50% of the male population aged between 50 and 60 years and further increases with advancing age.

Moreover, with increased raised life expectancy, it is obvious that the treatment of prostatic hypertrophy is also of growing importance from a social viewpoint since this condition weighs heavily on national health costs and limits working activity due to the particular symptomatology (pollakiuria, strangury, nocturia). The not infrequent occurrence of ascending infections, which further complicate the general picture, it also to be considered.

Hitherto, it can be said that prostatic hypertrophy has best been dealt with surgically rather than medically in view of the uncertainty which still remains with regard to hormonal therapy. This, no doubt, reflects the dualism existing with regard to the pathogenesis of the hypertrophic process, ascribed by some authors to hyperoestrogenism and by others to androgen hyperproduction following hypophysis stimulation.

From the therapeutic point of view, this has entailed the adoption of widely differing methods of treatment and the use of widely differing kinds of substances with not always comparable results. Currently, androgen therapy is no longer used very much because there are potential risks that a possible carcinoma, coexisting in the hyperplastic context, might be neoplastically activated.

Furthermore, treatment with oestrogens, which is still widely used, can induce feminisation processes, as well as testicular atrophy and squamous epithelial hyperplasia of the posterior urethral tract.

Hormonal therapy, besides directly acting on the prostate itself, thus also induces a number of highly undesirable side effects, particularly after prolonged therapy.

This justifies the search for new, non-hormonal substances which are capable of selectively acting on the prostate without interfering with other parenchyma.

Recently, new hypotheses is the field of benign prostatic hypertrophy have been advanced. First, histochemical studies on human material from autopsies showed a significant increase (approximately 80%) of prostatic cholesterol in subjects with BPH or prostatic neoplasia.

It was also observed that, in rats, the prostate synthesises nearly as much cholesterol as the liver, although it lacks a feed-back mechanism similar to that of the liver and, therefore, it is liable to cholesterol surcharge, resulting in glandular congestion with reactive hyperplasia.

Bearing in mind these observations and the fact that partricin derivatives, like other polyene substances or even more so, are endowed with a marked hypocholesterol activity due to the inhibition of reabsorption of the exogenous pool cholesterol at gastrointestinal tract level (see U.S. Patent Application Ser. No. 910,951) an expermental control was carried out to ascertain the activity of the derivatives in question on benign prostatic hypertrophy.

Following a preliminary screening, which demonstrated that practically all partricin derivatives were endowed with a good basic activity, although sometimes accompanied by signs of gastric intolerance, a more detailed clinical study was carried out with mepartricin, which is less toxic and better tolerated by the oral route compounds, due to the necessity of having to carry out a prolonged therapy without causing harmful side effects. Mepartricin, which is not absorbed gastroenterically and, therefore, acts exclusively at a topical level, gave the highest hypocholesterol efficacy.

SUMMARY OF THE INVENTION

The present invention provides a method for the treatment of benign prostatic hypertrophy in human males, comprising administering an active compound selected from the group consisting of partricin, $C_1$–$C_6$ alkyl ester of partricin and $C_1$–$C_6$ alkyl ester of N-mono- and N,N-disubstituted partricin, the N-substituents being $C_1$–$C_6$ alkyl or carboxylic acyl, to a human male in need of said treatment in an amount sufficient to alleviate benign prostatic hypertrophy.

The active compound used according to the present invention can, if desired, be administered in the form of a water-soluble complex with a complex-forming compound selected from the group consisting of benzalkonium chloride, sodium lauryl sulphate, sodium tetradecyl sulphate, sodium desoxycholate and sodium dehydrocholate, the weight ratio of active compound to complex-forming compound in the water-soluble complex being from 1:1 to 1:10, preferably from 1:1 to 1:5 and more preferably from 1:1 to 1:2.

DETAILED DESCRIPTION OF THE INVENTION

A trial has been carried out on 20 patients aged between 51 and 86, with benign prostatic hyperplasia in 3 different phases of evolution:

Group 1: cases with slight asymptomatic hyperplasia ascertained by bladder catheterisation and rectal exploration.

Group 2: cases with chronic hyperplasia diagnosed both clinically and radiologically, with or without chronic urinary retention.

Group 3: cases with acute urinary retention.

In order the better to ascertain a possible dose-effect relationship, two different posologic schemes were devised, involving administering 100,000 Units/day to 10 subjects (1 gastroresistant tablet containing 50,000 Units of mepartricin every 12 hours) and 150,000 Units/day to the other 10 subjects (1 gastroresistant tablet containing 50,000 Units of mepartricin every 8 hours) for a period of 30 consecutive days.

The results were evaluated according to objective and subjective parameters, noting, in particular, the following symptoms: pollakiuria and nocturia, dysuria and strangury, force and calibre of the stream and residual urine.

Before beginning the treatment, a radiopaque cystography was systemically carried out.

Evolution of the hyperplastic process was followed by serial controls every 10 days. Cystography was repeated in each case just after termination of the treatment. In 3 cases, it was possible to carry out a follow-up control after 5 to 6 months.

The overall clinical evaluation was as follows:

Excellent: resolution of clinical symptomatology and evident reduction of the prostatic shadow in the post-treatment control cystography.

Satisfactory: disappearance of urinary symptoms but no marked improvement in cystographic findings.

Nil: no appreciable clinical or radiographic improvement.

Tolerance to the drug was ascertained, especially with regard to manifestations of gastric intolerance, since mepartricin is not absorbed, as well as the control of certain haematochemical parameters.

RESULTS

The findings are reported in the following Table 1. In all cases, frequency disturbances were improved by the treatment, nocturia frequency showing a mean decrease of 65% compared with pre-treatment, while pollakiuria decreased by about 25%.

On the 20th day of treatment, dysuria and strangury had disappeared in 17 patients but were still present, albeit much reduced, in 3 patients. At the end of the treatment, all patients were symptom-free. The force and calibre of the stream progressively increased while all subjects with residual urine (15 cases) found that this condition gradually improved and finally subsided. This improvement was more rapid and marked in the patients treated with 150,000 U/day.

At the end of treatment, it was possible to carry out bladder catheterisation more easily, even when using, in some cases, large catheters, whereas before treatment, this manoeuvre had always been difficult. From a purely clinical point of view, this finding demonstrates a reduced prostatic size which is clearly due to the treatment.

The evolution of the radiological findings, especially where prostatic impairment was greater, was particularly informative, always verifying a regression or, even more often, a complete disappearance of prostatic shadow.

The 3 cases controlled 5 to 6 months after treatment had ended showed a stable therapeutic result, without apparent recurrence of the hyperplastic process.

In all, 14 "excellent" results and 6 "satisfactory" results were obtained (see the following Table 2).

The best results were seen in cases of slight hypertrophy (initial lesion), with disappearance of urinary symptomatology and a return to normal of the prostate size; moderately severe cases came next. After a short treatment cycle with mepartricin, patients with acute urinary retention had spontaneous diuresis with concomitant, more or less pronounced, reduction of the hyperplastic process.

Mepartricin tolerance was entirely satisfactory with the exception of 2 cases who experienced transient gastric pyrosis and nausea during the first week which spontaneously subsided without discontinuing or changing the posology. During treatment, the usual blood examinations (haemoglobin, glycaemia, BUN, SGOT, SGPT) showed no significant changes compared with the initial findings.

It can, therefore, be concluded that mepartricin has a selective and powerful action on the prostatic glandular epithelium with consequent resolution of the hyperplastic processes, tolerance being entirely satisfactory in long-term treatment.

In the light of the above findings, a new method is provided for the treatment of BPH, based on the administration of mepartricin or of other partricin derivatives.

With particular regard to oral administration, which is the preferred although not the only route for long-term treatment, pharmaceutical formulations have also been developed, these being described in the following Examples:

EXAMPLE 1.

Each tablet contains:

| | |
|---|---|
| mepartricin | 50,000 U |

-continued

| | | |
|---|---|---|
| starch | | 40 mg. |
| sodium citrate | | 30 mg. |
| talc | | 10 mg. |
| magnesium stearate | | 5 mg. |
| lactose | q.s. ad | 280 mg. |

EXAMPLE 2.

Each gastroresistant tablet contains:

| | | |
|---|---|---|
| mepartricin | | 50,000 U |
| starch | | 40 mg. |
| sodium citrate | | 30 mg. |
| talc | | 10 mg. |
| magnesium stearate | | 5 mg. |
| lactose | q.s. ad | 280 mg. |
| shellac | | 1.5 mg. |
| cellulose acetate phthalate | | 9 mg. |
| diethyl phthalate | | 5.5 mg. |
| talc | | 9 mg. |

EXAMPLE 3.

One gram of granulate for an oral suspension contains:

| | |
|---|---|
| mepartricin | 50,000 U |
| sodium citrate | 0.03 g. |
| precipitated silica | 0.01 g. |

-continued

| | | |
|---|---|---|
| sodium carboxymethylamide | | 0.09 g. |
| cocoa powder | | 0.01 g. |
| cocoa fluid extract | | 0.01 g. |
| powdered sucrose | q.s. ad | 1 g. |

Water is added to the dry granulate powder (25 ml. per 5 g. of product); thus, 1 ml. of oral suspension contains 10,000 U of mepartricin.

EXAMPLE 4.

Each gastroresistant tablet contains:

| | | |
|---|---|---|
| mepartricin/sodium lauryl sulphate complex (1:2 w/w) | | 50,000 U |
| starch | | 40 mg. |
| sodium chloride | | 30 mg. |
| sodium citrate | | 30 mg. |
| magnesium stearate | | 5 mg. |
| microgranular cellulose | q.s. ad | 360 mg. |
| gastroresistant coating | q.s. ad | 385 mg. |

The present invention is not limited to the above-described pharmaceutical formulations. Thus, for example, for oral administration, use can be made of all types of dosage units, such as tablets, dragees, hard gelatine capsules, syrups and the like.

Other administration routes and relative formulations (suppositories, injectable preparations and the like) may also be used for an effective clinical treatment.

TABLE 1

Evolution of the nocturia and pollakiuria (a), dysuria and strangury (b), force and calibre of stream (c) and residual urine (d) in a group of 20 patients with prostatic hypertrophy treated orally for 30 days with 100,000 U/day (cases 1–10) and with 150,000 U/day (cases 11–20) of mepartricin.

| Case No. | Age (years) | Symptoms | Pretreatment | After 10 days | After 20 days | After 30 days |
|---|---|---|---|---|---|---|
| 1 | 67 | Nocturia | 3–4 | 3 | 1 | 1 |
| | | Pollakiuria | 9–10 | 9 | 8 | 8 |
| | | Dysuria | 3 | 2 | absent | absent |
| | | Strangury | 2 | 1 | absent | absent |
| | | Force and calibre of stream | — | — | + | + |
| | | Residual urine | 200 | 200 | 100 | absent |
| 2 | 86 | Nocturia | 4–5 | 3–4 | 2 | 1 |
| | | Pollakiuria | 8–10 | 9 | 7 | 7 |
| | | Dysuria | 3 | 3 | 1 | absent |
| | | Strangury | 3 | 2 | absent | absent |
| | | Force and calibre of stream | — | — | + | + |
| | | Residual urine | 300 | 300 | 80 | absent |
| 3 | 51 | Nocturia | 3 | 2 | 1 | 1 |
| | | Pollakiuria | 8 | 8 | 7 | 6 |
| | | Dysuria | 1 | absent | absent | absent |
| | | Strangury | absent | absent | absent | absent |
| | | Force and calibre of stream | — | — | + | + |
| | | Residual urine | absent | absent | absent | absent |
| 4 | 64 | Nocturia | 3 | 3 | 2 | 1 |
| | | Pollakiuria | 8 | 8 | 7 | 6 |
| | | Dysuria | 2 | 1 | absent | absent |
| | | Strangury | absent | absent | absent | absent |
| | | Force and calibre of stream | — | — | + | + |
| | | Residual urine | 100 | 100 | absent | absent |
| 5 | 64 | Nocturia | 3 | 2 | 1 | 1 |
| | | Pollakiuria | 8 | 8 | 7 | 7 |
| | | Dysuria | 1 | 1 | absent | absent |
| | | Strangury | absent | absent | absent | absent |
| | | Force and calibre of stream | — | — | + | + |
| | | Residual urine | absent | absent | absent | absent |
| 6 | 68 | Nocturia | 3 | 3 | 1 | — |
| | | Pollakiuria | 7 | 5 | 2 | 2 |
| | | Dysuria | 2 | 1 | absent | absent |
| | | Strangury | absent | absent | absent | absent |
| | | Force and calibre of stream | — | — | + | + |
| | | Residual urine | absent | absent | absent | absent |
| 7 | 65 | Nocturia | 3 | 3 | 2 | 1 |
| | | Pollakiuria | 8–9 | 8 | 7 | 6 |

TABLE 1-continued

Evolution of the nocturia and pollakiuria (a), dysuria and strangury (b), force and calibre of stream (c) and residual urine (d) in a group of 20 patients with prostatic hypertrophy treated orally for 30 days with 100,000 U/day (cases 1-10) and with 150,000 U/day (cases 11-20) of mepartricin.

| Case No. | Age (years) | Symptoms | Pretreatment | After 10 days | After 20 days | After 30 days |
|---|---|---|---|---|---|---|
| | | Dysuria | 2 | 1 | absent | absent |
| | | Strangury | 1 | 1 | absent | absent |
| | | Force and calibre of stream | — | — | + | + |
| | | Residual urine | 80 | 80 | absent | absent |
| 8 | 61 | Nocturia | 4 | 3 | 2 | 1 |
| | | Pollakiuria | 10 | 10 | 8 | 7 |
| | | Dysuria | 1 | 1 | absent | absent |
| | | Strangury | 1 | 1 | 1 | absent |
| | | Force and calibre of stream | — | — | + | + |
| | | Residual urine | absent | absent | absent | absent |
| 9 | 69 | Nocturia | 2-3 | 2 | 2 | 1 |
| | | Pollakiuria | 8 | 8 | 8 | 7 |
| | | Dysuria | 1 | 1 | absent | absent |
| | | Strangury | 1 | absent | absent | absent |
| | | Force and calibre of stream | — | — | + | + |
| | | Residual urine | 230 | 230 | 170 | absent |
| 10 | 62 | Nocturia | 3 | 3 | 2 | 1 |
| | | Pollakiuria | 8-9 | 8 | 7 | 6 |
| | | Dysuria | 1 | 1 | 1 | absent |
| | | Strangury | absent | absent | absent | absent |
| | | Force and calibre of stream | — | — | + | + |
| | | Residual urine | absent | absent | absent | absent |
| 11 | 78 | Nocturia | retention | 3 | 2 | 2 |
| | | Pollakiuria | retention | 8 | 6 | 6 |
| | | Dysuria | 3 | 1 | absent | absent |
| | | Stangury | 3 | 1 | absent | absent |
| | | Force and calibre of stream | retention | — | + | + |
| | | Residual urine | retention | 250 | 100 | absent |
| 12 | 84 | Nocturia | 3 | 3 | 2 | 2 |
| | | Pollakiuria | 8 | 8 | 7 | 6 |
| | | Dysuria | 2 | absent | absent | absent |
| | | Strangury | 1 | absent | absent | absent |
| | | Force and calibre of stream | — | + | + | + |
| | | Residual urine | 300 | 200 | 100 | absent |
| 13 | 70 | Nocturia | 3 | 2 | 1 | 1 |
| | | Pollakiuria | 8 | 7 | 6 | 6 |
| | | Dysuria | 1 | absent | absent | absent |
| | | Strangury | absent | absent | absent | absent |
| | | Force and calibre of stream | — | + | + | + |
| | | Residual urine | 190 | 50 | absent | absent |
| 14 | 68 | Nocturia | 3 | 3 | 2 | 1 |
| | | Pollakiuria | 9 | 9 | 8 | 6 |
| | | Dysuria | 2 | absent | absent | absent |
| | | Strangury | 1 | absent | absent | absent |
| | | Force and calibre of stream | — | + | + | + |
| | | Residual urine | 300 | 200 | absent | absent |
| 15 | 63 | Nocturia | retention | 3 | 2 | 2 |
| | | Pollakiuria | retention | 8 | 8 | 7 |
| | | Dysuria | 2 | 1 | absent | absent |
| | | Strangury | 2 | absent | absent | absent |
| | | Force and calibre of stream | retention | — | + | + |
| | | Residual urine | retention | 350 | 100 | absent |
| 16 | 78 | Nocturia | 3 | 2 | 1 | 1 |
| | | Pollakiuria | 8 | 7 | 7 | 6 |
| | | Dysuria | 1 | absent | absent | absent |
| | | Strangury | absent | absent | absent | absent |
| | | Force and calibre of stream | — | + | + | + |
| | | Residual urine | 100 | absent | absent | absent |
| 17 | 61 | Nocturia | 3 | 2 | 2 | 1 |
| | | Pollakiuria | 8 | 7 | 7 | 6 |
| | | Dysuria | 1 | absent | absent | absent |
| | | Strangury | — | — | — | — |
| | | Force and calibre of stream | — | + | + | + |
| | | Residual urine | 350 | 290 | 80 | absent |
| 18 | 64 | Nocturia | 3 | 2 | 2 | 2 |
| | | Pollakiuria | 8 | 7 | 7 | 7 |
| | | Dysuria | 2 | absent | absent | absent |
| | | Strangury | absent | absent | absent | absent |
| | | Force and calibre of stream | — | + | + | + |
| | | Residual urine | 100 | absent | absent | absent |
| 19 | 70 | Nocturia | 3 | 2 | 2 | 1 |
| | | Pollakiuria | 8 | 7 | 7 | 6 |
| | | Dysuria | 1 | absent | absent | absent |
| | | Strangury | absent | absent | absent | absent |
| | | Force and calibre of stream | — | + | + | + |
| | | Residual urine | 50 | absent | absent | absent |

TABLE 1-continued

Evolution of the nocturia and pollakiuria (a), dysuria and strangury (b), force and calibre of stream (c) and residual urine (d) in a group of 20 patients with prostatic hypertrophy treated orally for 30 days with 100,000 U/day (cases 1-10) and with 150,000 U/day (cases 11-20) of mepartricin.

| Case No. | Age (years) | Symptoms | Pretreatment | After 10 days | After 20 days | After 30 days |
|---|---|---|---|---|---|---|
| 20 | 74 | Nocturia | 3 | 3 | 2 | 2 |
|  |  | Pollakiuria | 9 | 8 | 8 | 7 |
|  |  | Dysuria | 2 | absent | absent | absent |
|  |  | Strangury | 1 | absent | absent | absent |
|  |  | Force and calibre of stream | — | + | + | + |
|  |  | Residual urine | 180 | 150 | absent | absent |

(a) Expressed as daily mean frequency
(b) Evaluated according to the following: absent; slight=1; moderate=2; serious=3
(c) Expressed as: increased = (+); decreased = (−)
(d) Measured in ml.

TABLE 2

Summary of clinical-radiological results obtained with a group of patients with prostatic hyperplasia treated with mepartricin administered by the oral route

| Total number of cases | Treatment | Groups | No. of cases | Clinical-radiological result | | |
|---|---|---|---|---|---|---|
|  |  |  |  | Excellent | Satisfactory | Nil |
| 20 | 10 cases (100,000 U/die) | I | 4 | 3 | 1 | — |
|  |  | II | 3 | 2 | 1 | — |
|  |  | III | 3 | 1 | 2 | — |
|  | 10 cases (150,000 U/die) | I | 3 | 3 | — | — |
|  |  | II | 5 | 3 | 2 | — |
|  |  | III | 2 | 2 | — | — |
|  | TOTALS |  |  | 14 | 6 | — |

We claim:

1. A method for the treatment of benign prostatic hypertrophy in human males, comprising administering an active compound selected from the group consisting of partricin, $C_1$–$C_6$ alkyl ester of partricin and $C_1$–$C_6$ alkyl ester of N-mono- and N,N-disubstituted partricin, the N-substituents being $C_1$–$C_6$ alkyl or carboxylic acyl, to a human male in need of said treatment in an amount sufficient to alleviate benign prostatic hypertrophy.

2. A method for the treatment of benign prostatic hypertrophy in human males, comprising administering methyl partricin to a human male in need of said treatment in an amount sufficient to alleviate benign prostatic hypertrophy.

3. A method for the treatment of benign prostatic hypertrophy in human males, comprising administering a water-soluble complex containing methyl partricin and sodium lauryl sulphate in a weight ratio of 1:2 to a human male in need of said treatment in an amount sufficient to alleviate benign prostatic hypertrophy.

4. A method for the treatment of benign prostatic hypertrophy in human males, comprising administering an active compound selected from the group consisting of partricin, $C_1$–$C_6$ alkyl ester of partricin and $C_1$–$C_6$ alkyl ester of N-mono- and N,N-disubstituted partricin, the N-substituents being $C_1$–$C_6$ alkyl or carboxylic acyl, in the form of a water-soluble complex with a complex-forming compound selected from the group consisting of benzalkonium chloride, sodium lauryl sulphate, sodium tetradecyl sulphate, sodium desoxycholate and sodium dehydrocholate, the weight ratio of active compound to complex-forming compound in the water-soluble complex being from 1:1 to 1:10, to a human male in need of said treatment in an amount sufficient to alleviate benign prostatic hypertrophy.

5. A method for the treatment of benign prostatic hypertrophy in human males, comprising administering methyl partricin in the form of a water-soluble complex with a complex-forming compound selected from the group consisting of benzalkonium chloride, sodium lauryl sulphate, sodium tetradecyl sulphate, sodium desoxycholate and sodium dehydrocholate, the weight ratio of methyl partricin to complex-forming compound in the water-soluble complex being from 1:1 to 1:10, to a human male in need of said treatment in an amount sufficient to alleviate benign prostatic hypertrophy.

* * * * *